United States Patent [19]

Fozzard

[11] B 3,996,299
[45] Dec. 7, 1976

[54] FLUORO COMPOUND PREPARATION
[75] Inventor: George B. Fozzard, Bartlesville, Okla.
[73] Assignee: Phillips Petroleum Company, Bartlesville, Okla.
[22] Filed: Feb. 8, 1973
[21] Appl. No.: 330,736
[44] Published under the second Trial Voluntary Protest Program on February 3, 1976 as document No. B 330,736.
[52] U.S. Cl. .............................. 260/648 F; 260/900
[51] Int. Cl.$^2$ ......................................... C07C 23/06
[58] Field of Search ................................ 260/648 F
[56] References Cited
UNITED STATES PATENTS

| | | |
|---|---|---|
| 2,957,032 | 10/1960 | Hauptschein et al. .......... 260/648 F |
| 3,662,009 | 5/1972 | Hutchinson ................... 260/648 F |
| 3,767,820 | 10/1973 | Holdsworth et al. ........... 260/648 F |
| 3,789,088 | 1/1974 | Lalande, Jr. et al. .......... 260/648 F |

OTHER PUBLICATIONS
Holdsworth et al., Chemical Abstracts, 77 74884c (1972).

Primary Examiner—D. Horwitz

[57] ABSTRACT

Compounds of the formulas

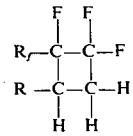 and 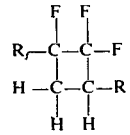

and mixtures thereof are prepared by codimerization of $R_f$-CF=CF$_2$ and R-CH=CH$_2$. The cleavage product of the cyclobutane derivative is copolymerized.

3 Claims, 1 Drawing Figure

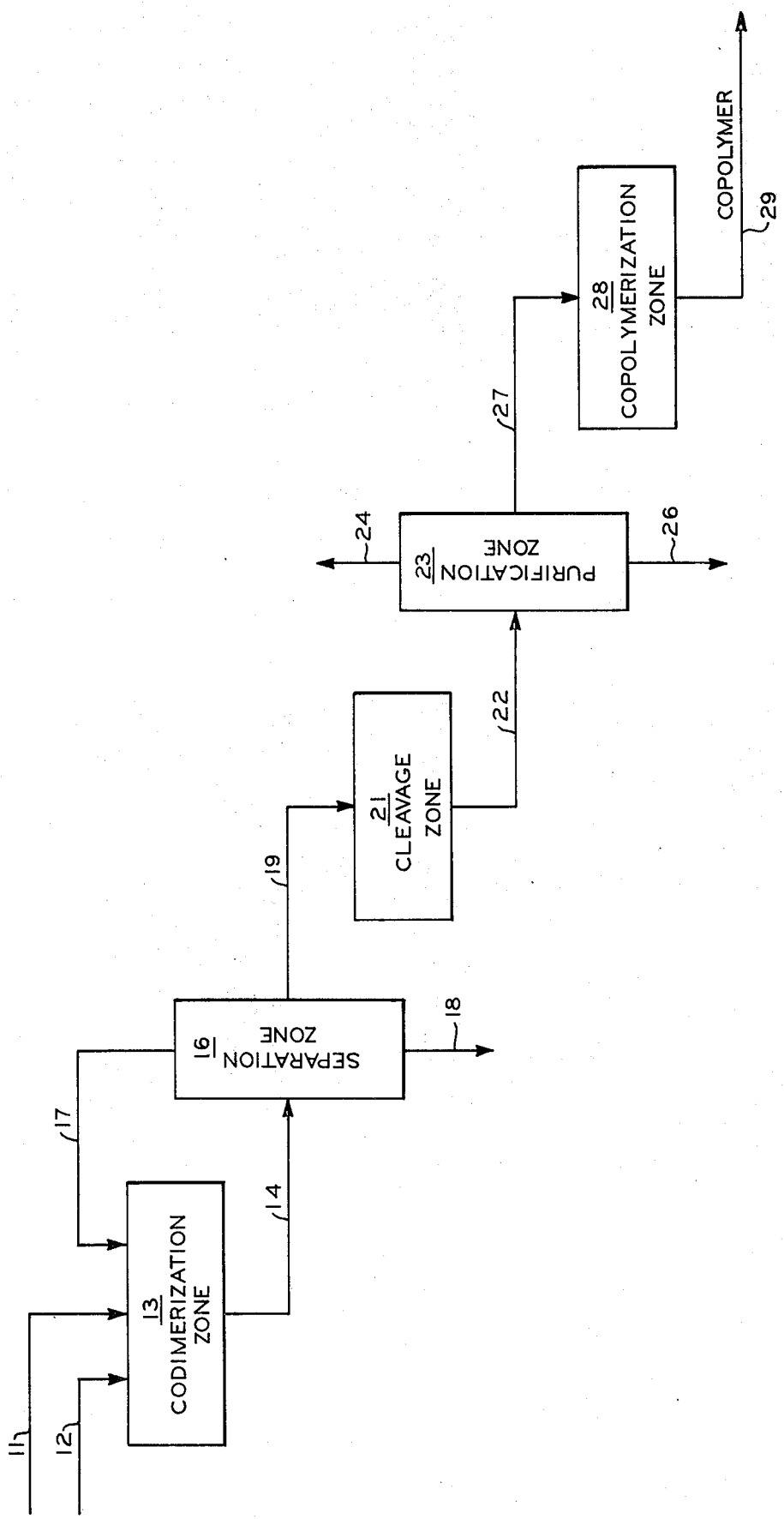

FLUORO COMPOUND PREPARATION

This invention relates to novel fluoro compounds. In one aspect the invention relates to the preparation of novel codimers. In another aspect the invention relates to cleavage of a cyclobutane derivative and to the copolymerization of the cleavage products.

Despite their relatively high cost, a number of fluorine-containing products are presently commercially available and some of these enjoyed a large degree of commercial success. However, because of relatively high cost, many fluorine-containing compounds, such as highly chemical-resistant fluoro polymers for example, are used in highly critical applications where their relatively high cost can be more readily justified and absorbed.

It is desirable, therefore, to find new fluorine-containing products and alternate methods of producing known highly desirable fluorine-containing products. As an example, a presently premium priced copolymer which has been stated to be useful in elastomer and sealant compositions, is the copolymer produced from approximately equimolar amounts of vinylidine fluoride and 2,3,3,3-tetrafluoropropylene. Although the vinylidene fluoride is readily available by a number of processes, 2,3,3,3-tetrafluoropropylene previously has been prepared only with relative difficulty.

It has now been found that the above-mentioned 2,3,3,3-tetrafluoropropylene can be prepared by an alternative route. Moreover, the new method of preparation is particularly suitable for the preparation of the copolymer with vinylidene fluoride because the new method produces, simultaneously, substantial amounts of vinylidene fluoride and the tetrafluoropropylene.

The alternative route includes the use of a new compound, 1-trifluoromethyl-1,2,2-trifluorocyclobutane. The thermal cracking of this cyclic material produces both vinylidene fluoride and 2,3,3,3-tetrafluoropropylene in approximately equimolar amounts. By the practice of the present invention other analogous and related cyclic products can be produced and cracked to other useful monomers and mixtures of monomers.

According to this invention there is produced a new composition of matter which is a compound of the formula

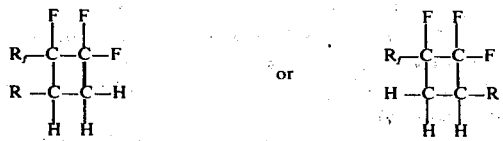

and mixtures thereof wherein each $R_f$ is a perfluoroalkyl radical, preferably having 1–10, more preferably 1–3, carbon atoms, and wherein skeletal branching, if present, is no closer than the 2-position with respect to the carbon atom to which it is attached; and wherein each R is selected from hydrogen or an unbranched alkyl radical, preferably an unbranched alkyl radical having 1–10 carbon atoms, but more preferably R is hydrogen.

The novel compounds are produced by the cyclocodimerization of a perfluoroolefin having the formula $R_f$—CF=CF$_2$ with a terminal monoolefin having the formula R—CH=CH$_2$, under suitable reaction conditions to produce the fluorine-containing cyclodimer. These novel compounds are those which can be visualized as occurring from the codimerization of the perfluoroolefin and the terminal monoolefin according to either possible mode of combination, i.e., either

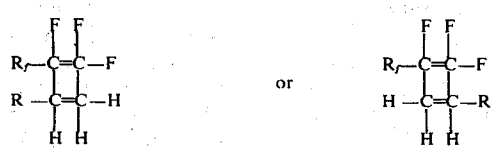

wherein $R_f$ and R are the same as defined above with respect to the compound. In a specific embodiment, a mixture of perfluoropropylene and ethylene is converted to 1-trifluoromethyl-1,2,2-trifluorocyclobutane.

Some examples of suitable perfluoroolefins used as comonomers to prepare the cyclocodimer of the present invention are perfluoropropylene, perfluorobutene-1, perfluoropentene-1, perfluoroheptene-1, perfluoro-4-ethylhexene-1, perfluorodecene-1, and mixtures of one or more of such perfluoroolefins. Some examples of suitable terminal monoolefins for use as comonomers are ethylene, propylene, butene-1, hexene-1, octene-1, decene-1, and mixtures thereof. Examples of codimers which can be prepared from the above include 1-trifluoromethyl-1,2,2-trifluorocyclobutane, 1-pentafluoroethyl-1,2,2-trifluorocyclobutane, 1-(perfluoro-n-hexyl)-1,2,2-trifluorocyclobutane, 1-trifluoromethyl-4-methyl-1,2,2-trifluorocyclobutane, and 1-trifluoromethyl-3-methyl-1,2,2-trifluorocyclobutane.

The novel codimers of the present invention are prepared by subjecting a suitable mixture of an applicable perfluoroolefin and an applicable terminal monoolefin to cyclodimerization conditions. Such conditions commonly include a reaction temperature in the range of 200°–600°C., preferably 300°–400°C. The reaction can be carried out at any convenient pressure, preferably at an elevated pressure which is as high as can be handled conveniently in the reaction apparatus being utilized. For example, pressures in the range of 0–10,000 psig are suitable. Preferably the pressures are in the range of 100–1000 psig considering both efficiency of the reaction and the cost of equipment necessary to withstand the pressure.

The cyclocodimerization reaction of the present invention is a bimolecular reaction and therefore approximately equimolar amounts of the comonomers can be utilized. However, preferably a molar excess, more preferably a substantial excess, of the terminal monoolefin is used. Broadly, the ratio of the monoolefin to the perfluoroolefin usually is in the range of 0.1:1 to about 100:1 preferably 1:1 to about 10:1.

The reaction time varies depending upon the temperature and pressure but normally is in the range of about 4 to about 1000 hours, preferably 10 to 100 hours.

Any convenient suitable dimerization apparatus can be used and the process can be carried out either batchwise or continuously. At the completion of the reaction period, the reaction mixture can be subjected to any suitable separation procedures to separate and isolate the desired products. For example, fractionation can be used to separate the more volatile unconverted comonomers from the cyclocodimer product and some small amounts of heavy materials which may have been produced. Generally, there is some free hydrogen fluoride present at the completion of the reaction and this can be removed by suitable washing and/or neutralization with an inorganic base. Unconverted comonomers can be recycled to the reaction zone.

As noted above, the novel cyclocodimers of this invention can be cracked to produce a mixture of acyclic fluorine-containing olefins which can be used as monomers and/or comonomers in polymerization reactions to produce useful polymeric materials. The cracking can be carried out at any suitable temperature. Temperatures in the range of 500°–1000°C. generally are suitable, preferably temperatures in the range of 600°–700°C. Any convenient pressure can be used but relatively low pressures favor the cracking operation and pressures near atmospheric are particularly preferred. The cracking reaction is relatively rapid and can be carried out continuously by passage through a heated reactor tube maintaining a contact time in the range of 0.01–10 seconds.

It has been found that at least minor amounts of such olefinic cracked products can be obtained by subjecting the original comonomers, perfluoropropylene and ethylene for example, to such cracking conditions. It appears that, under such conditions, small amounts of the cyclocodimer are formed and this cyclic material then undergoes the cleavage reaction to form new fluorine-containing olefinic compounds. However, yields on such a one step process are poor and the cracking of previously prepared cyclocodimer gives much better results.

The drawing is a diagrammatic flow sheet illustrating one embodiment of the process of the invention.

A suitable perfluoroolefin is fed through pipe 11 and a suitable terminal monoolefin through pipe 12 to the cyclocodimerization zone 13. Suitable conditions are maintained in zone 13 for production of the cyclocodimer. The effluent from cyclocodimerization zone 13 is fed through pipe 14 to separation zone 16. The lighter comonomers are recycled through pipe 17 to cyclocodimerization zone 13 and any heavier by-products removed through pipe 18. The cyclocodimer is fed through pipe 19 into cleavage or cracking zone 21. In zone 21 conditions are maintained suitable for producing the desired cleavage or cracking reaction resulting in the production of the new fluorine-containing olefinic compounds. The effluent from cracking zone 21 is fed through pipe 22 to purification zone 23. In zone 23 any lighter impurities are removed through pipe 24 and heavier impurities through pipe 26 while the acyclic fluorine-containing olefins produced in cleavage zone 21 are fed through pipe 27 to copolymerization zone 28. Although in most instances it may be desirable to remove impurities from the effluent stream from cleavage zone 21, it is not necessary to separate the new acyclic fluorine-containing olefins which can be fed without separation from each other directly to the copolymerization zone 28. The resulting copolymer is removed through pipe 29.

In a specific operation according to the process illustrated in the drawing perfluoropropylene is introduced into cyclocodimerization zone 13 (a stirred autoclave) through pipe 11 while ethylene is introduced into cyclocodimerization zone 13 through pipe 12 such that the mol ratio of ethylene to perfluoropropylene is about 5:1.

In cyclocodimerization zone 13 a temperature of 350°C. is maintained for 24 hours at a pressure of from about 500–200 psig.

The reaction mixture in cyclocodimerization zone 13 is transferred to a distillation tower as separation zone 16. The lower boiling unreacted ethylene and perfluoropropylene are flashed overhead and recycled to cyclocodimerization zone 13 through pipe 17. The cyclocodimer product is next taken from the distillation tower and transferred through pipe 19 to cleavage zone 21, a cylindrical heated reactor. The heavier distillation tower by-product bottoms are removed from the distillation tower through pipe 18.

The cyclocodimer product is contacted in cleavage zone 21 at 600°C. under atmospheric pressure for about 0.1 minute.

The effluent from the cracking zone 21 is fed through pipe 22 to another distillation tower as purification zone 23. Said effluent is fractionally distilled to remove lighter impurities overhead through pipe 24. The mixture of vinylidene fluoride and 2,3,3,3,-tetrafluoropropylene is next recovered from the distillation tower and transferred to copolymerization zone 28 through pipe 27. Heavy residues from the fractional distillation in purification zone 23 are removed through pipe 26.

The mixture of vinylidene fluoride and 2,3,3,3-tetrafluoropropylene is polymerized in a stirred pressure vessel as polymerization zone 28. The copolymerization is conducted in an aqueous emulsion with hydrogen peroxide as the polymerization catalyst at a temperature of 80°C. under about 300 psig pressure for about 8 hours. The polymerization reactor is cooled to room temperature and vented to the atmosphere and the polymeric product is coagulated with a small amount of dilute hydrochloric acid. The coagulum is removed by pipe 29 to a vessel for separation of the polymer from the coagulum and washing of said recovered polymer.

EXAMPLE I

Into a 3000 ml stainless steel cylindrical reactor were charged 110 g (about 0.73 moles) of hexafluoropropylene and 28 g (about 1 mole) of ethylene. The reactor and contents was then heated for about 69 hours at 350°C. and at a pressure which was about 470 psig at the beginning of the reaction period and was about 180 psig at the completion of the reaction period.

At the conclusion of the reaction period, the reactor was cooled, vented through a chilled condenser to permit the escape of most of the volatile residual comonomers, and washed to remove free hydrofluoric acid. The yield of crude product was 111.2 g. The crude product was distilled and 64.49 g of 1-trifluromethyl-1,2,2-trifluorocyclobutane was recovered. This amounted to a 49.5 percent yield based on the charge of hexafluoropropylene.

The distilled product was found to have boiling point (uncorrected) of 68.9°C. Elemental analysis of this material gave the following results:

|  | Carbon | Hydrogen |
| --- | --- | --- |
| Theory | 33.72 | 2.26 |
| Found | 33.9 | 2.3 |

A sample of the material examined by nuclear magnetic resonance (NMR). The $H^1$ and $F^{19}$ spectra of this material were found to be consistent with the indicated structure. The following interpretations were made from the spectra.

The proton spectrum showed a complex resonance centered at −145 Hz (−110 to −180 Hz). The reference spectrum of 1,1,2,2-tetrafluorocyclobutane was similarly centered about the same chemical shift position and it had a very symmetrical appearance. The trifluoromethyl compound had a more complex appearance on the downfield side, as might be expected for this unsymmetrical compound. A minor impurity was indicated by the —CH₃ resonance observed at —55 Hz.

The fluorine spectrum showed a "singlet" produced by the —CF₃ group. The CF₃—CF— coupling was small, 10 Hz or less, and the spectrometer used did not have this resolution, consequently a "single" resonance was observed. Upfield were four peaks representing the AB pattern of the —CF₂— group with a coupling of about 200 Hz, which was consistent with the average coupling constants for geminal fluorine atoms in tetrafluorocyclobutanes reported in the literature. Further upfield was the broad unresolved resonance of the —CF group. As stated above, the —CF—CF₃ coupling was small as was the —CF—CF₂— coupling and therefore a single broad resonance for the —CF groups was seen.

A mass spectrogram of the material was also consistent with the indicated structure.

EXAMPLE II

Into a 1000 ml stainless steel cylindrical reactor was charged 36 g (about 0.24 moles) of hexafluoropropylene and 9.6 g (about 0.344 moles) of ethylene. The reactor was then heated for about 4 days at an inside temperature of about 260°C. for 3.5 days then at 325°C. for 0.5 days at pressures which varied in the range of 450 to 340 psig.

At the completion of the reaction period, the reactor was allowed to cool. It was then vented through a dry ice/Freon trap and the crude product was washed with water. The crude yield (some heavies were present) of 1-trifluoromethyl-1,2,2-trifluorocyclobutane was 36.40 g (theory was 42.7 g).

In a similar manner perfluoroheptene-1 was reacted with ethylene at 325°C. for about 16 hours and hexafluoropropylene was reacted under similar conditions with propylene. Results similar to, but less effective than the results obtained in the reaction of hexafluoropropylene and ethylene were obtained in both instances.

EXAMPLE III

In this example, the novel compound 1-trifluoromethyl-1,2,2-trifluorocyclobutane was cracked to 2,3,3,3-tetrafluoropropylene and vinylidene fluoride. Using a helium carrier gas, the cyclocodimer was vaporized and passed into a hot tube reactor maintained at 600°C. and at about atmospheric pressure. The residence time in the reaction zone was about 0.1 minute. A total of 51.12 g of the cyclocodimer was passed through the reactor of which 89 percent was converted. The crude product was distilled and 18.71 g (65 percent distilled yield) of 2,3,3,3-tetrafluoropropylene was recovered.

What is claimed is:
1. As a new composition of matter a compound of the formula

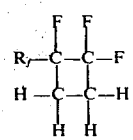

and mixtures thereof wherein $R_f$ is a perfluoroalkyl radical having 1–10 carbon atoms per molecule and wherein skeletal branching, if present, is no closer than the 2-position with respect to the carbon atom to which it is attached.

2. The composition of claim 1 wherein $R_f$ has 1–3 carbon atoms per molecule.

3. A composition according to claim 1 which is 1-trifluoromethyl-1,2,2-trifluorocyclobutane.

* * * * *